United States Patent
Madej et al.

(10) Patent No.: US 11,812,987 B2
(45) Date of Patent: Nov. 14, 2023

(54) CUTTING BALLOON CATHETER

(71) Applicant: BOSTON SCIENTIFIC SCIMED, INC., Maple Grove, MN (US)

(72) Inventors: Alyssa Madej, Minnetonka, MN (US); Amelia Ann Sandberg, Fridley, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 156 days.

(21) Appl. No.: 17/102,927

(22) Filed: Nov. 24, 2020

(65) Prior Publication Data

US 2021/0153891 A1   May 27, 2021

Related U.S. Application Data

(60) Provisional application No. 62/941,413, filed on Nov. 27, 2019.

(51) Int. Cl.
*A61M 25/10* (2013.01)
*A61B 17/3207* (2006.01)
(Continued)

(52) U.S. Cl.
CPC ...... *A61B 17/320725* (2013.01); *A61B 17/22* (2013.01); *A61L 29/06* (2013.01); *A61M 25/104* (2013.01); *A61B 2017/00951* (2013.01); *A61B 2017/00955* (2013.01); *A61B 2017/22001* (2013.01); *A61B 2017/22051* (2013.01); *A61M 25/10* (2013.01); *A61M 2025/109* (2013.01); *A61M 2025/1086* (2013.01)

(58) Field of Classification Search
CPC ............ A61B 17/320725; A61B 17/22; A61B 2017/00951; A61B 2017/00955; A61B 2017/22001; A61B 2017/22051; A61B 17/12022; A61B 17/12027; A61B 17/12031; A61B 17/12036; A61B 17/1204; A61B 17/12045; A61B 17/12099; A61B 17/12; A61B 17/12104; A61B 17/12109; A61B 17/12113; A61B 17/12118; A61B 17/12122; A61B 2017/1212; A61B 17/12131; A61B 17/12136; A61M 25/104; A61M 2025/1086; A61M 2025/109; A61M 2025/1084

See application file for complete search history.

(56) References Cited

U.S. PATENT DOCUMENTS 5,320,634 A * 6/1994 Vigil ............... A61B 17/320725
                                                  604/103.08
6,500,186 B2   12/2002 Lafontaine et al.
(Continued)

OTHER PUBLICATIONS

International Search Report and Written Opinion dated Feb. 18, 2021 for International Application No. PCT/US2020/061967.

*Primary Examiner* — Timothy J Neal
*Assistant Examiner* — Mitchell Brian Hoag
(74) *Attorney, Agent, or Firm* — Seager, Tufte & Wickhem LLP

(57) ABSTRACT

An example cutting balloon is disclosed. The example cutting balloon includes an expandable member having an outer surface and longitudinal axis, a first cutting member disposed along the outer surface of the expandable member and a covering encapsulating the expandable member and the first cutting member.

17 Claims, 8 Drawing Sheets

(51) Int. Cl.
*A61B 17/22* (2006.01)
*A61L 29/06* (2006.01)
*A61B 17/00* (2006.01)

(56) References Cited

U.S. PATENT DOCUMENTS

| | | | |
|---|---|---|---|
| 6,562,062 B2 | 5/2003 | Jenusaitis et al. | |
| 6,632,231 B2 | 10/2003 | Radisch | |
| 6,746,463 B1 | 6/2004 | Schwartz | |
| 6,808,531 B2 | 10/2004 | Lafontaine et al. | |
| 6,951,566 B2 | 10/2005 | Lary | |
| 7,011,670 B2 | 3/2006 | Radisch, Jr. | |
| 7,029,483 B2 | 4/2006 | Schwartz | |
| 7,153,315 B2 | 12/2006 | Miller | |
| 7,172,609 B2 | 2/2007 | Radisch, Jr. | |
| 7,338,463 B2* | 3/2008 | Vigil | A61B 17/320725 604/96.01 |
| 7,413,558 B2 | 8/2008 | Kelley et al. | |
| 7,494,497 B2 | 2/2009 | Weber | |
| 7,799,043 B2* | 9/2010 | O'Brien | A61B 17/22 606/159 |
| 8,491,615 B2* | 7/2013 | Manderfeld | B29C 65/48 606/167 |
| 8,585,959 B2* | 11/2013 | Burton | A61M 25/104 606/190 |
| 8,870,816 B2* | 10/2014 | Chambers | A61M 25/104 604/103.05 |
| 9,242,076 B2* | 1/2016 | Burton | A61M 25/10 |
| 9,302,071 B2 | 4/2016 | Manderfeld et al. | |
| 9,603,619 B2 | 3/2017 | Bence et al. | |
| 10,182,841 B1* | 1/2019 | Rousu | A61B 17/320725 |
| 10,729,892 B2* | 8/2020 | Yamazaki | A61M 29/02 |
| 11,020,142 B2* | 6/2021 | Gunderson | A61M 25/104 |
| 11,154,320 B2* | 10/2021 | Haverkost | A61M 25/1002 |
| 11,166,742 B2* | 11/2021 | Schneider | A61M 25/0082 |
| 11,338,115 B2* | 5/2022 | Slattery | A61B 17/320725 |
| 2003/0163148 A1 | 8/2003 | Wang et al. | |
| 2004/0133223 A1* | 7/2004 | Weber | A61M 29/02 606/159 |
| 2005/0070888 A1 | 3/2005 | Dimatteo et al. | |
| 2005/0119678 A1 | 6/2005 | O'Brien et al. | |
| 2005/0137615 A1 | 6/2005 | Mapes et al. | |
| 2005/0137618 A1 | 6/2005 | Kunis | |
| 2005/0149102 A1 | 7/2005 | Radisch et al. | |
| 2005/0288629 A1 | 12/2005 | Kunis | |
| 2006/0111736 A1 | 5/2006 | Kelley | |
| 2006/0116700 A1 | 6/2006 | Crow | |
| 2006/0116701 A1 | 6/2006 | Crow | |
| 2006/0129093 A1 | 6/2006 | Jackson | |
| 2006/0135980 A1 | 6/2006 | Trinidad | |
| 2006/0247674 A1 | 11/2006 | Roman | |
| 2007/0016232 A1 | 1/2007 | St. Martin et al. | |
| 2007/0060863 A1 | 3/2007 | Goeken et al. | |
| 2007/0213752 A1 | 9/2007 | Goodin et al. | |
| 2009/0240270 A1* | 9/2009 | Schneider | A61M 25/104 606/198 |
| 2011/0082489 A1* | 4/2011 | Davies, Jr. | A61M 25/10 606/192 |
| 2013/0284352 A1* | 10/2013 | Manderfeld | A61M 25/0009 156/245 |
| 2014/0343590 A1 | 11/2014 | Solem et al. | |
| 2015/0151092 A1 | 6/2015 | Davies et al. | |
| 2015/0297281 A1* | 10/2015 | Sutermeister | A61M 25/0043 606/49 |
| 2019/0307992 A1 | 10/2019 | Haverkost et al. | |

\* cited by examiner

CUTTING BALLOON CATHETER

CROSS REFERENCE TO RELATED APPLICATIONS

This application claims the benefit of U.S. Provisional Patent Application Ser. No. 62/941,413 filed on Nov. 27, 2019, the disclosure of which is incorporated herein by reference.

TECHNICAL FIELD

The disclosure pertains to angioplasty balloon catheters having cutting elements mounted onto an angioplasty balloon. More particularly, the disclosure is directed to preventing cutting balloon blade delamination on an angioplasty cutting balloon

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences as the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter.

Evidence has shown that cutting or scoring a stenosis with an angioplasty balloon equipped with a cutting element (during an angioplasty treatment procedure, for example) may reduce incidences of re-stenosis. Accordingly, angioplasty balloons equipped with cutting elements having cutting edges have been developed to attempt to enhance angioplasty treatments. In some instances, the stress placed upon the cutting elements may result in delamination of one or more portions of the cutting balloon. Therefore, there is a need for improved structures and methods to preventing cutting blade delamination on angioplasty cutting balloons.

BRIEF SUMMARY

This disclosure provides design, material, manufacturing methods, and use alternatives for medical devices. An example cutting balloon includes an expandable member having an outer surface and longitudinal axis, a first cutting member disposed along the outer surface of the expandable member and a covering encapsulating the expandable member and the first cutting member.

Alternatively or additionally to any of the embodiments above, wherein the covering is fixedly attached to the expandable member, the first cutting member or both the expandable member and the first cutting member.

Alternatively or additionally to any of the embodiments above, wherein the covering has a thickness between 5 μm and 35 μm.

Alternatively or additionally to any of the embodiments above, wherein the covering includes a thermoplastic polyurethane.

Alternatively or additionally to any of the embodiments above, further comprising a plurality of fiber members attached to the expandable member.

Alternatively or additionally to any of the embodiments above further comprising a mounting pad and an attachment material, wherein the attachment material attaches the mounting pad to the outer surface of the expandable member, wherein the first cutting member is attached to the mounting pad, and wherein the covering encapsulates the cutting member, the mounting pad and the attachment material.

Alternatively or additionally to any of the embodiments above, wherein the attachment material is selected from the group comprising ultra-violet curable adhesive, two-part epoxy and thermoplastic polyurethane.

Alternatively or additionally to any of the embodiments above, wherein the mounting pad includes a thermoplastic polyurethane.

Alternatively or additionally to any of the embodiments above, wherein the covering encapsulates the cutting member, the mounting pad, the attachment material and a portion of the outer surface of the expandable member extending away from the mounting pad.

Alternatively or additionally to any of the embodiments above, wherein the covering and the mounting pad are configured to form a monolithic structure.

Alternatively or additionally to any of the embodiments above, wherein the expandable member is configured to shift from a first configuration to an expanded configuration, and wherein the covering encapsulates the first cutting member in both the first configuration and the expanded configuration.

Alternatively or additionally to any of the embodiments above, further comprising a second cutting member disposed along the outer surface of the expandable member, wherein the second cutting member is axially aligned with the first cutting member, and wherein the coating encapsulates the first cutting member, the second cutting member and the expandable member.

Alternatively or additionally to any of the embodiments above, further comprising a mounting pad attached to the outer surface of the expandable member, wherein the first cutting member and the second cutting member are both attached to the mounting pad.

Alternatively or additionally to any of the embodiments above, wherein the covering is configured to prevent the cutting member from releasing from the outer surface of the expandable member.

Another example cutting balloon includes an expandable member having an outer surface and a longitudinal axis, the expandable member configured to shift between a first configuration to a second expanded configuration. The cutting balloon also includes a cutting member assembly attached to the outer surface of the expandable member. The cutting member assembly includes an attachment material disposed along the outer surface of the expandable member, a mounting pad attached to the attachment material and a cutting blade attached to the mounting pad. Further, the cutting balloon also includes a covering fixedly attached to both the expandable member and the cutting member assembly, wherein the covering surrounds both the expandable member and the cutting member assembly as the expandable member shifts between the first configuration and the second configuration.

Alternatively or additionally to any of the embodiments above, wherein the covering is configured to prevent the cutting member from releasing from the outer surface of the expandable member.

Alternatively or additionally to any of the embodiments above, wherein the covering has a thickness between 5 μm and 35 μm.

Alternatively or additionally to any of the embodiments above, wherein the covering includes a thermoplastic polyurethane.

Alternatively or additionally to any of the embodiments above, wherein the covering and the mounting pad are configured to form a monolithic structure.

An example method of treating a body lumen includes advancing a cutting balloon to a target site in the body lumen, wherein the cutting balloon includes an expandable member having an outer surface and longitudinal axis, a first cutting member disposed along the outer surface of the expandable member and a covering encapsulating the expandable member and the first cutting member. The method also includes expanding the expandable member such that the cutting member engages the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
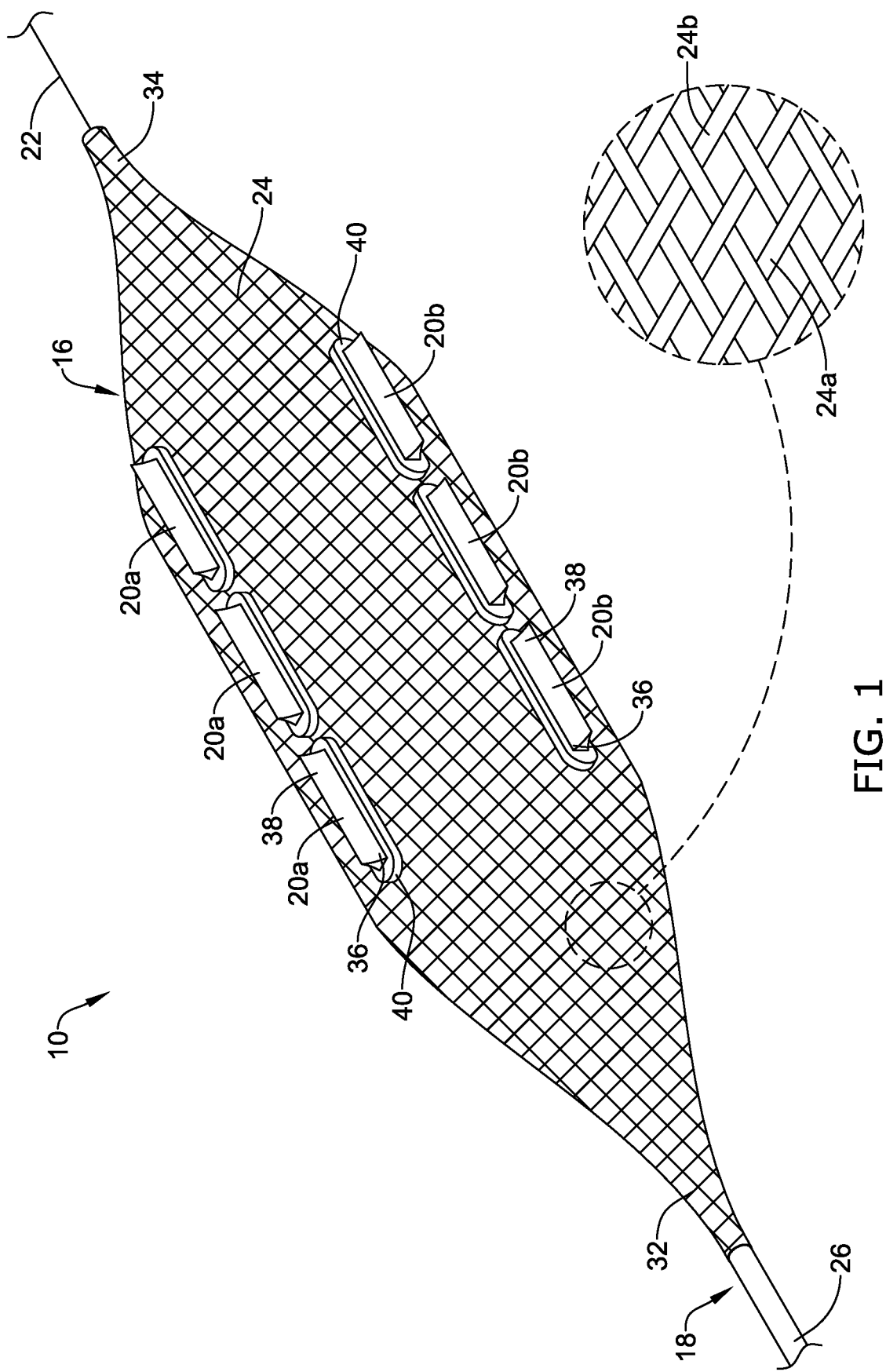
FIG. 1 is a perspective view of an example cutting balloon.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

FIG. 1 is a perspective view of an example cutting balloon catheter 10. The catheter 10 may include a balloon 16 coupled to a catheter shaft 18. One or more cutting members or blades 20a/20b may be mounted on the balloon 16. In general, the catheter 10 may be advanced over a guidewire 22, through the vasculature, to a target lesion. Once positioned at the target location in the vasculature, the balloon 16 may be inflated such that the balloon and/or the cutting members exert a radially outward force on the lesion. When the cutting members 20 engage the lesion, they may cut or score the lesion to facilitate enlarging the body lumen in which the lesion is located. It is contemplated that the cutting balloon catheter 10 may be used to treat any lumen in the body, including any peripheral or cardiac lumen for which a lesion has developed.

The cutting members 20a/20b may vary in number, position, and arrangement about the balloon 16. For example, the catheter 10 may include one, two, three, four, five, six, seven, eight, nine, ten, eleven, twelve or more cutting members 20a/20b that are disposed at any position along the balloon 16 and in a regular, irregular, or any other suitable pattern. For example, in some embodiments the balloon 16 may include a plurality of cutting members longitudinally aligned at various points around the circumference of the balloon 16. For example, the balloon 16 shown in FIG. 1 illustrates three cutting members 20a aligned along the longitudinal axis of the balloon 16. Additionally, FIG. 1 illustrates three different cutting members 20b aligned along the longitudinal axis of the balloon 16, whereby the cutting members 20b are circumferentially offset from the cutting members 20a. Each of the three cutting members 20a may be spaced away from one another along the longitudinal axis of the balloon 16. Similarly, each of the three cutting members 20b may be spaced away from one another along the longitudinal axis of the balloon 16.

In some examples, the cutting members 20a/20b may be made from any suitable material such as a metal, metal alloy, polymer, metal-polymer composite, and the like, or any other suitable material. For example, the cutting members 20a/20b may be made from stainless steel, titanium, nickel-titanium alloys, tantalum, iron-cobalt-nickel alloys, or other metallic materials.

The balloon 16 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyetherester, polyester, polyamide, elastomeric polyamides, polyether block amide (PEBA), Pebax 7233 as well as other suitable materials, or mixtures, combinations, copolymers thereof, polymer/metal composites, and the like. The shaft 18 may be a catheter shaft, similar to typical catheter shafts. For example, the catheter shaft 18 may include an outer tubular member 26 and an inner tubular member (not shown in FIG. 1) extending through at least a portion of the outer tubular member 26. The outer tubular member 26 and the inner tubular member may be made of metals, metal alloys, polymers, metal-polymer composites or any other suitable materials.

In some embodiments the inner tubular member may be disposed coaxially within the outer tubular member 26. In some embodiments, the inner and outer tubular members may or may not be secured to one another along the longitudinal axis of the catheter shaft 18. Alternatively, the inner tubular member may follow an inner wall of the outer tubular member 26 or otherwise be disposed adjacent the inner wall of the outer tubular member 26.

The inner tubular member may include an inner lumen (not shown in FIG. 1). In at least some embodiments, the inner lumen of the inner tubular member may be a guidewire lumen for receiving the guidewire 22 therethrough. Accordingly, the catheter 10 can be advanced over the guidewire 22 to a desired target location in the body. In some examples, the guidewire lumen may extend along the entire length of the catheter shaft 18 such that catheter 10 resembles a traditional "over-the-wire" catheter. Alternatively, the guidewire lumen 28 may extend along only a portion of the catheter shaft 18 such that the catheter 10 resembles a "single-operator-exchange" or "rapid-exchange" catheter.

It can be appreciated that the space between the outer surface of the inner tubular member and the inner surface of the outer tubular member 26 catheter shaft 18 may permit inflation media to flow into and out of the balloon 16 to inflate and/or deflate the balloon 16.

It can further be appreciated that, in some examples, the catheter shaft 18 may be constructed as a "multi-lumen" shaft, in which a single shaft includes multiple lumen extending therein, rather than having an inner tubular member extending within a lumen of an outer tubular member, as described above.

The balloon 16 may be coupled to the catheter shaft 18 in any of a number of suitable ways. For example, the balloon 16 may be adhesively or thermally bonded to the catheter shaft 18. In some embodiments, a proximal waist 32 of the balloon 16 may be bonded to the catheter shaft 18, for example, bonded to the distal end of the outer tubular member 26, and a distal waist 34 of the balloon 16 may be bonded to the catheter shaft 18, for example, bonded to the distal end of the inner tubular member 24. The exact bonding positions, however, may vary.

FIG. 1 illustrates one possible arrangement of the cutting members 20a/20b mounted to the balloon 16. While the balloon 16 is shown having three cutting members 20a and three cutting members 20b mounted thereon, in other embodiments, the balloon 16 may include one, two, three, four, five, six, seven, eight, nine, ten, eleven, twelve or more cutting members. The cutting members 20a/20b may be symmetrically or asymmetrically spaced around the circumference of the balloon 16. Further, the cutting members 20a/20b may include a base portion 36 and a cutting edge 38 opposite the base portion 36, whereby the cutting edge 38 extends radially outward from the balloon 16.

The cutting members 20a/20b may be secured to the outer surface of the balloon 16 by attaching the base portion 36 of each of the cutting members 20a/20b in a mounting pad 40 and adhesively bonding the mounting pad 40 (with the base portion 36 of the cutting member 20 attached thereto), to the outer surface of the balloon 16 with an adhesive material. As illustrated in FIG. 1, in some examples, each of the cutting members 20a/20b may be attached to its own, discrete mounting pad 40. As shown, each mounting pad 40 may be separated from one another. However, in other examples, all of the cutting members 20a may be mounted to a single mounting pad 40 which may extend along the length of all the cutting members 20a. Similarly, in some examples, all of the cutting members 20b may be mounted to a single mounting pad 40 which may extend along the length of all the cutting members 20b.

FIG. 1 further illustrates that the cutting balloon 10 may include one or more fibers 24 disposed along the outer surface of the balloon 16. In particular, the detailed view of FIG. 1 illustrates that the fibers 24 may include a first fiber 24a and a second fiber 24b which are wound, braided, twisted, weaved, wrapped, etc. around the outer surface of the balloon 16. In other examples, the fibers 24 may be positioned just below the outer surface of the balloon 16, whereby each of the fibers 24 (e.g., the first fiber 24a and the second fiber 24b) are encased in the material utilized to construct the wall of the balloon 16.

While FIG. 1 illustrates that the balloon fibers 24 may include a first fiber 24a and a second fiber 24b, this is not intended to be limiting. Rather, in some instances, the balloon fibers 24 may include one, two, three, four, five, six, seven, eight or more individual balloon fibers which are wound, braided, twisted, weaved, wrapped, etc. around the outer surface of the balloon 16.

It can be appreciated affixing the balloon fibers 24 to the outer surface (or embedded within the wall thickness) of the balloon 16 may limit the degree to which the balloon 16 elongates when inflated to a given pressure. For example, it can be appreciated that the fibers 24 may be designed with limited elongation properties, and therefore, counteract the tendency of the polymer balloon to elongate when inflated to a given pressure.

In some examples, the balloon fibers 24 may include continuous reinforcement members. In other examples, the balloon fibers 24 may include intermittent reinforcement members. For example, in some examples the balloon fibers 24 may extend continuously along the entire length of the balloon 16, while in other examples the balloon fibers 24 may extend only along a portion of the length of the balloon 16. It can be appreciated that the balloon fibers 24 may be oriented along the balloon 16 in a variety of configurations.

The balloon fibers 24 may be constructed from a suitable material which restricts the elongation of the balloon 16 at a given pressure. For example, the balloon fibers 24 may be constructed from polyester, polyamide, carbon fiber, ceramic materials, graphite, various metals, or combinations thereof.

The balloon fibers 24 may be used in filamentary form or may be used in the form of a yarn or as a fabric of plain weave, satin weave, twill weave, basket weave, braid, winding or the like. In some examples, the fibers 24 may include parallel aligned continuous fibers 24 extending along the surface of or embedded with the polymer balloon wall. Additionally, in some examples, the fibers 24 may be bonded together with the polymer used to construct the balloon 16.

As discussed above, the fibers 24 may be embedded or layered onto the polymer used to construct the balloon 16 and oriented longitudinally. The fibers 24 may be distributed evenly throughout the balloon 16 thereby reinforcing the entire balloon 16. In some embodiments, the fibers 24 may be concentrated in various regions of the balloon 16.

Figure 2:
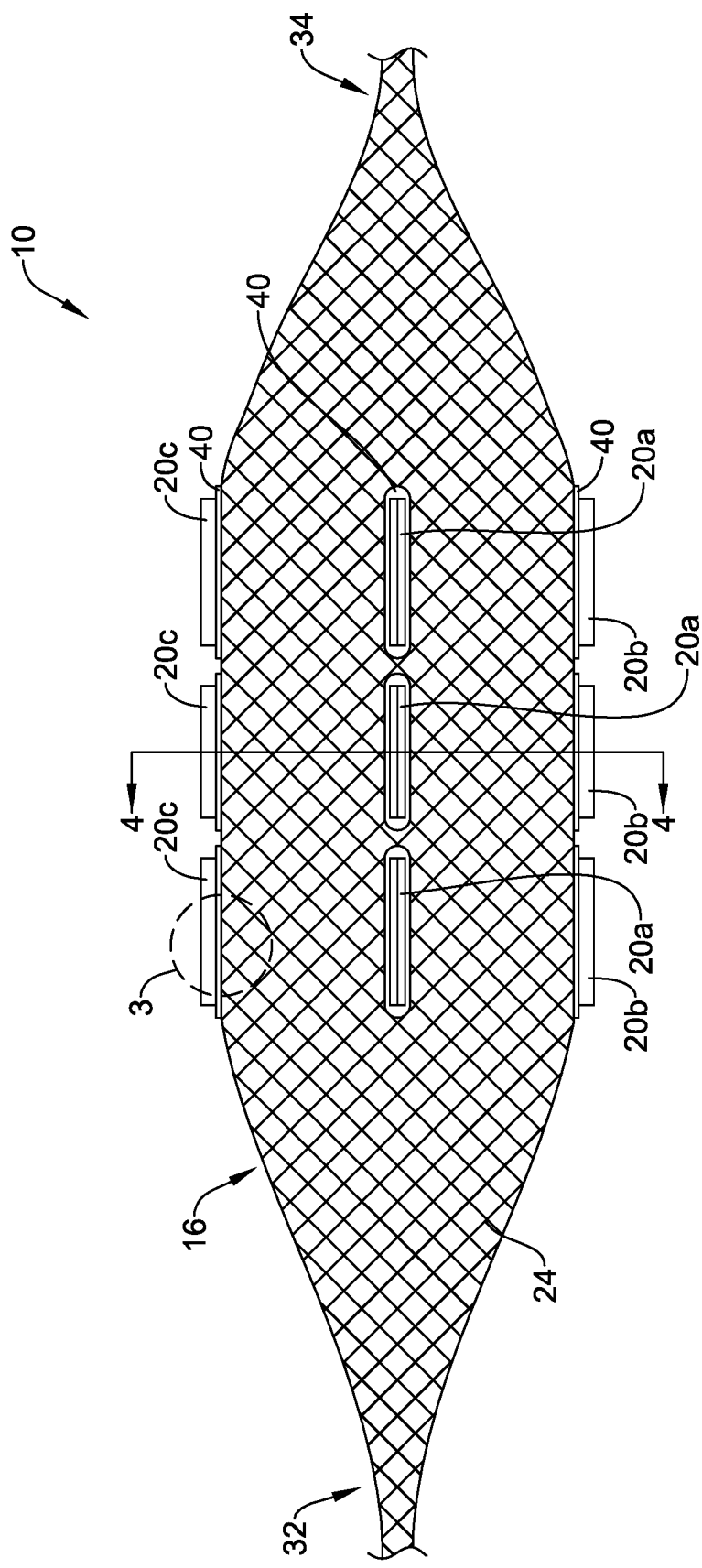
FIG. 2 is a side view of the example cutting balloon show in FIG. 1.

FIG. 2 illustrates a side view of the example cutting balloon 10 shown in FIG. 1. In particular, FIG. 2 illustrates the cutting balloon including three cutting members 20a longitudinally aligned at a first circumferential location, three cutting members 20b longitudinally aligned at a second circumferential location and three cutting members 20c longitudinally aligned at a third circumferential location, whereby the first, second and third circumferential locations are offset from one another. In some examples, it can be appreciated the groups of cutting members 20a/20b/20c may be circumferentially offset from one another by approximately 90 degrees. To that end, it can be appreciated that the cutting balloon 10 may include a fourth group of cutting members which are offset 180 degrees from the three cutting members 20a (e.g., the fourth group of cutting members are not shown in FIG. 2 as they are hidden behind cutting members 20a in the page).

Additionally FIG. 2 illustrates each of the cutting members 20a/20b/20c embedded in a mounting pad 40, as described above. Further, FIG. 2 illustrates the fibers 24 extending along the balloon 16 from the proximal balloon waist 32 to the distal balloon waist 34, as described above.

Figure 3:
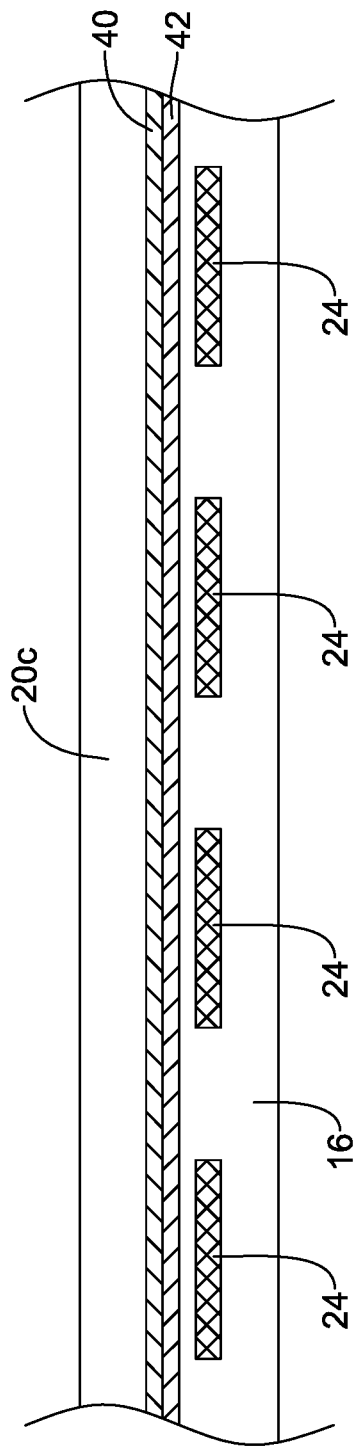
FIG. 3 illustrates the detailed view of FIG. 2.

FIG. 3 illustrates the detailed view 3 of FIG. 2. Specifically, FIG. 3 illustrates the example cutting member 20c attached to the example mounting pad 40, as described above. Further, FIG. 3 illustrates that the example mounting pad 40 may be attached to the balloon 16 via an adhesive 42. Further yet, FIG. 3 illustrates that the wall thickness of the balloon 16 may include one or more fibers 24 embedded therein. The one or more fibers 24 may be spaced apart from one another, as shown in FIG. 3. It can be appreciated that while FIG. 3 illustrates the one or more fibers 24 embedded with the wall of the balloon 16, it is also possible that, in some examples, the one or more fibers may be secured to the outer surface of the balloon 16.

In some examples, the mounting pad 40 may be formed from thermoplastic polyurethane (TPU). Further, in some examples, the adhesive utilized to attach the mounting pad 40 to the outer surface of the balloon may include an UV curable adhesive. However, in other examples, the adhesive utilized to attach the mounting pad 40 to the outer surface of the balloon may include a variety of adhesives, such as a thermoplastic polyurethane or two-part epoxies. For example, in some instances a mounting pad 40 constructed from thermoplastic polyurethane may be adhered to the balloon surface using thermoplastic polyurethane.

In some examples, the cutting balloon 10 may include a thermoplastic polyurethane coating over the top of the one or more fibers 24 (for example, in instances in which the fibers 24 are mounted to the surface of the balloon 16). Coating the fibers 24 in a thermoplastic polyurethane may improve the bonding of a thermoplastic polyurethane mounting pad 40 to the outer surface of the balloon 16.

Figure 4:
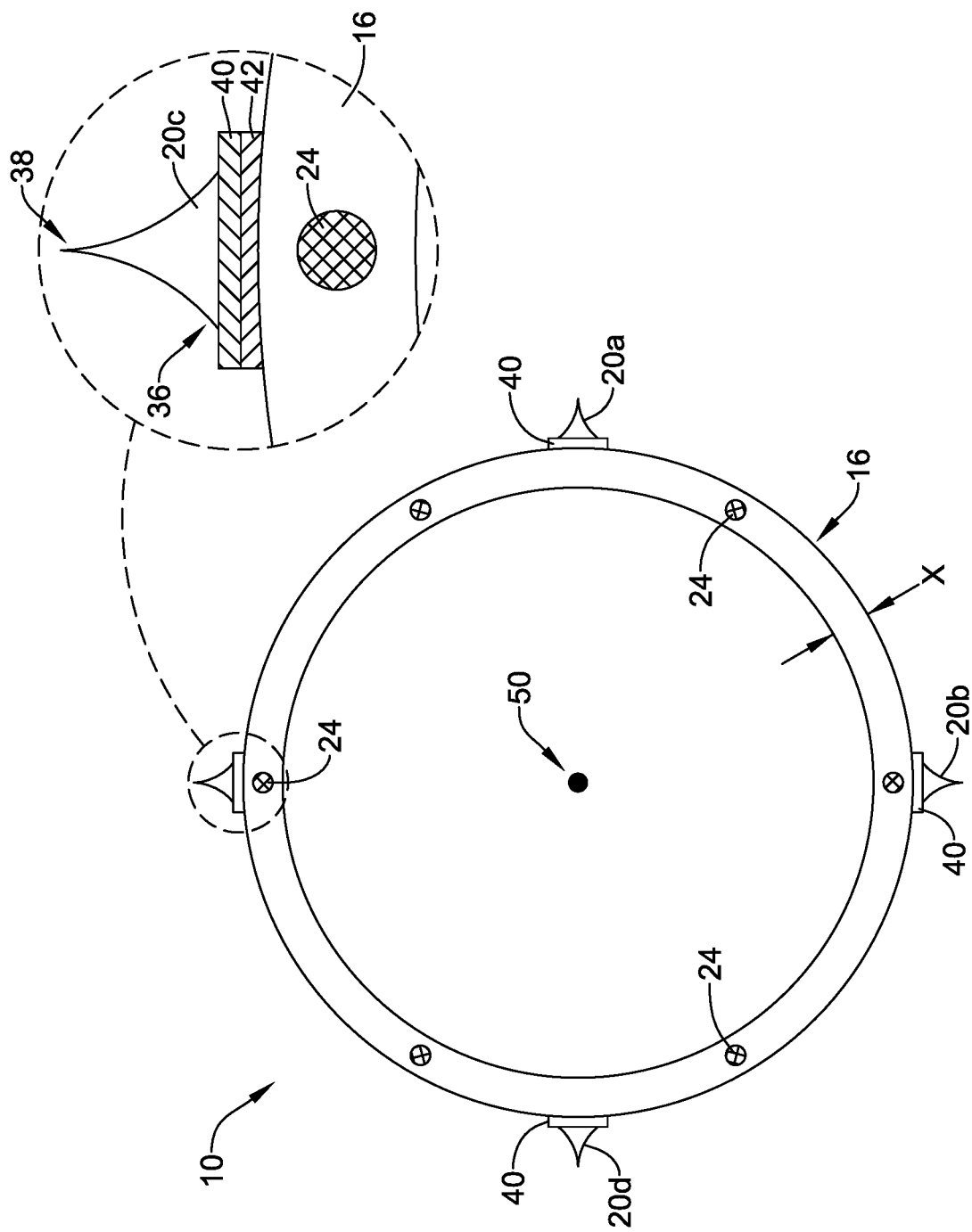
FIG. 4 is a cross-sectional view taken along line 4-4 of FIG. 2.

FIG. 4 is a cross-sectional illustration taken along line 4-4 of FIG. 2. FIG. 4 illustrates the cutting members 20a/20b/20c/20d spaced equidistant around the longitudinal axis 50 of the balloon member 16. While FIG. 4 illustrates the cutting members 20a/20b/20c/20d spaced equidistant around the longitudinal axis 50 of the balloon member 16, this is not intended to be limiting. Rather, it is contemplated that the cutting members 20a/20b/20c/20d may be spaced at any position relative to one another along the circumference of the balloon 16.

Further, the detailed view of FIG. 4 shows the cutting edge 38 of the cutting member 20a extending radially away from the central longitudinal axis 50 of the balloon 50. Further yet, the detailed view of FIG. 4 shows the base portion 36 of the cutting member 20a attached to the mounting pad 40. Additionally, FIG. 4 illustrates the mounting pad 40 attached to the outer surface of the balloon 16 via the adhesive 42 (e.g., adhesive, TPU, etc.). The adhesive 42 may be designed to couple the mounting pad 40 to the outer surface of the balloon 16. It can be appreciated from FIG. 4 that each of the cutting members 20a/20b/20c/20d may include a cutting edge 38, base portion 36, mounting pad 40 and adhesive 42 shown in the detailed view.

FIG. 4 further illustrates the fibers 24 embedded within the wall of the balloon 16. The wall thickness of the balloon 16 is depicted as dimension "X" in FIG. 4. As discussed above, in some examples, the fibers 24 may be fully encased in the wall of the balloon 16. However, in other examples, the fibers 24 may be positioned on the outer surface of the balloon 16. In such embodiments, the adhesive 42 may be designed to couple the mounting pad 40 to the outer surface of the balloon 16 and the fibers 24.

Figure 5:
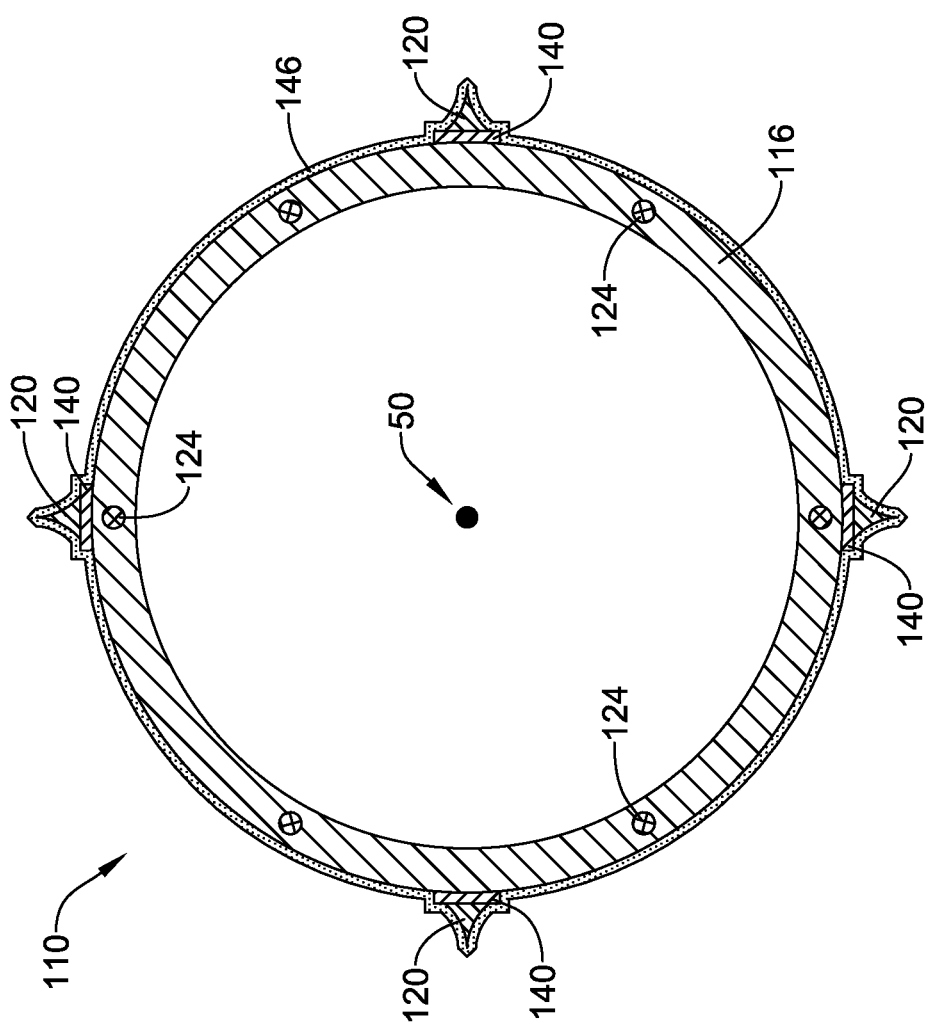
FIG. 5 is a cross-sectional view of another example cutting balloon.

FIG. 5 illustrates another example cutting balloon 110. The cutting balloon 110 may be similar in form and function to the cutting balloon 10 discussed above. For example the cutting balloon 110 may include cutting members 120 (similar to the cutting members 20a/20b/20c/20d discussed above) spaced equidistant around the longitudinal axis 50 of the balloon member 116 (similar to the balloon 16 discussed above). Further, each of the cutting members 120 may be attached to the balloon 116 via a mounting pad 140 and adhesive (not shown in FIG. 5). Further yet, FIG. 5 illustrates that the cutting balloon 110 may include fibers 124 (similar to the fibers 124 discussed above) embedded with the balloon 116. As discussed above with respect to the cutting balloon 10 above, the fibers 124 may be fully encased in the wall of the balloon 116. However, in other examples, the fibers 124 may be positioned on the outer surface of the balloon 116.

FIG. 5 further illustrates that, in some examples, at least a portion or, in some embodiments, substantially the entire cutting balloon 110 may include a covering 146 extending around the outer surface of the balloon 116, the cutting members 120, the mounting pads 140 and any other structure (e.g., fibers 124, adhesive, etc.) present on the outer surface of the balloon 116. In some examples, the covering 146 may include thermoplastic polyurethane TPU, parylene coating, thin-film coatings, or any other suitable material. Further, the thickness of the covering 146 may be from about 5 µm to 35 µm, or about 10 µm to 30 µm, or about 15 µm to 25 µm, or about 20 µm. As will be discussed in greater detail below, covering a portion of, or substantially the entire balloon 116, the cutting members 120, the mounting pads 140 and/or any other structure (e.g., fibers 124, adhesive, etc.) may substantially prevent the cutting members 120 from delaminating from the balloon 116.

In some examples, the covering 146 may be applied via a dip coating process, chemical vapor deposition, or other suitable process. In other words, the cutting balloon 110 may be dipped into a container of the covering 146 (e.g., a liquid resin of TPU or other suitable covering material), whereby the covering 146 is uniformly applied over the cutting balloon 110 (including the balloon 116 and all the structures attached thereto). After the dipping process, the covering 146 may be allowed to cure, thereby encapsulating the balloon 116 and all the structures attached thereto (the cutting members 120, the mounting pads 140, the fibers 124, adhesive, etc.) within the covering 146.

For the purposes of this disclosure, the word "encapsulate" may be understood to include examples in which one or more cutting members 120 are entirely covered, coated, surrounded, etc. by the covering 146. Additionally, the word "encapsulate" may be understood to include examples in which the surface (including the cutting edge) of one or more of the cutting members 120 are not exposed to the surrounding environment of the cutting members 120. "Encapsulate" may also be understood to include examples in which every surface of the cutting members 120 are covered by a surface of the covering 146. Additionally, in other examples, "encapsulate" may be understood to mean that the surfaces of the cutting members 120, the mounting pads 140 and only the portions of the balloon 116 adjacent to the mounting pad 140 are entirely covered (and thereby not exposed to the surrounding environment) by the coating 146. It can further be appreciated that, in some examples, "encapsulate" may include instances in which the mounting pad 140 and the covering 146 may be formed from the same material (e.g., thermoplastic polyurethane TPU) and, therefore, the cutting member 120 may be entirely surrounded by a monolithic material. In such instances, it can be appreciated that the term "encapsulated" may be understood to mean that the cutting member 120 is positioned within a cavity, pocket, chamber, etc. of a monolithic material. In yet other examples, the term "encapsulate" may include instances in which the entire balloon 116, the cutting members 120, the mounting pads 140, the fibers 124, the adhesive, and any other structures coupled to the balloon 116 are entirely covered by the covering 146.

Figure 6:
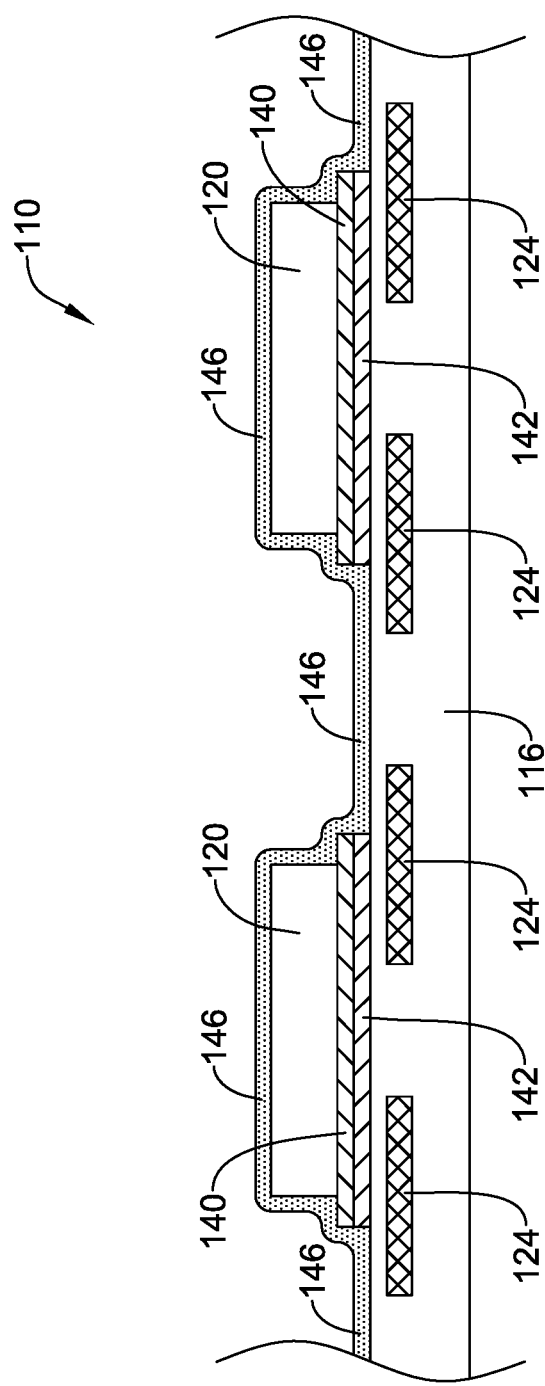
FIG. 6 is a side view of a portion of the cutting balloon shown in FIG. 5.

FIG. 6 illustrates a side view of a portion of the cutting balloon 110 shown in FIG. 5. For example, FIG. 6 illustrates two example cutting members 120 which are longitudinally aligned along the longitudinal axis of the balloon 116 (examples of multiple cutting members longitudinally aligned is shown in FIG. 1). Further, FIG. 6 illustrates each of the cutting members 120 coupled to a mounting pad 140, whereby each mounting pad 140 is attached to the outer surface of the balloon 116 via an adhesive 142 (e.g., TPU, an adhesive, etc.). Further yet, FIG. 6 illustrates the fibers 124 embedded in the wall of the balloon 116.

Figure 6A:
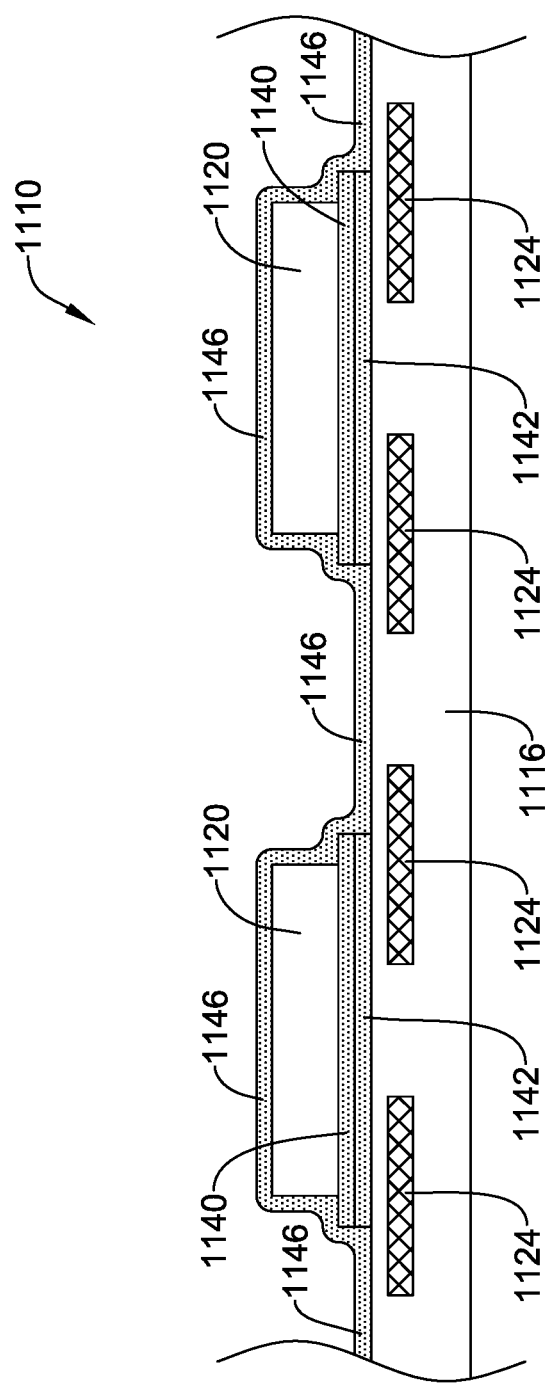
FIG. 6A is a side cross-sectional view of a portion of another embodiment of cutting balloon.

Additionally, FIG. 6A illustrates an embodiment of cutting balloon 1110 including a balloon 1116 with fibers 1124 similar to the balloon 110 described above, but where the cutting members 1120, the mounting pads 1140 and the adhesive 1142 are encapsulated in the covering 1146. In some examples, it can be appreciated that the covering material 1146 may be able to bond, attach, couple, melt, combine, etc. with the mounting pad 1140 and/or the adhesive 1142 (as shown, the covering material 1146 combines with the mounting pad 1140 and the adhesive 1142 to form a monolithic structure). This may occur, for example, when the covering material 1146, the mounting pad 1140, and the adhesive 1142 are formed from the same material. For example, in some instances, the covering material 1146, the mounting pad 1140, and the adhesive 1142 may be formed from TPU.

As discussed above, the combination of the covering material 146 and the mounting pad 140 and/or adhesive 142 (for example, if the covering material 146 mechanically or chemically bonds with the mounting pad 140 and/or the adhesive 142), may create a chamber, pocket, cavity, compartment, etc. within which the cutting member 120 may reside. In particular, if the cutting member 120 were to separate from the outer surface of the balloon 116 and/or the mounting pad 140 (e.g., due to delamination of the cutting member 120 from the balloon 116 and/or the mounting pad 140), the chamber bounded by the covering 146 and the mounting pad 140 and/or the adhesive 142 may prevent the cutting member 120 from tearing away from the balloon 116 and releasing into the vasculature of a patient. In other words, even if the cutting member were to separate from the balloon 116 (e.g., due to delamination at the point of contact with the mounting pad 140, adhesive 142 and/or the balloon 116) the covering 146, alone or in combination with the mounting pad 140, adhesive 142 and/or the balloon 116, continues to surround the cutting member 120, the mounting pad 140, the adhesive 142 and/or the balloon 116 when the balloon 116 is in an unexpanded and/or expanded configuration and may prevent the cutting member 120 from being released into the vasculature of a patient. Additionally, it can be appreciated that encapsulating the cutting members 120 and/or the mounting pad 140, adhesive 142, etc. within the covering 146 may increase the force required for delamination to occur by a factor of 10×, or about 20×, or about 30×, or about 40×, or about 50×.

Figure 7:
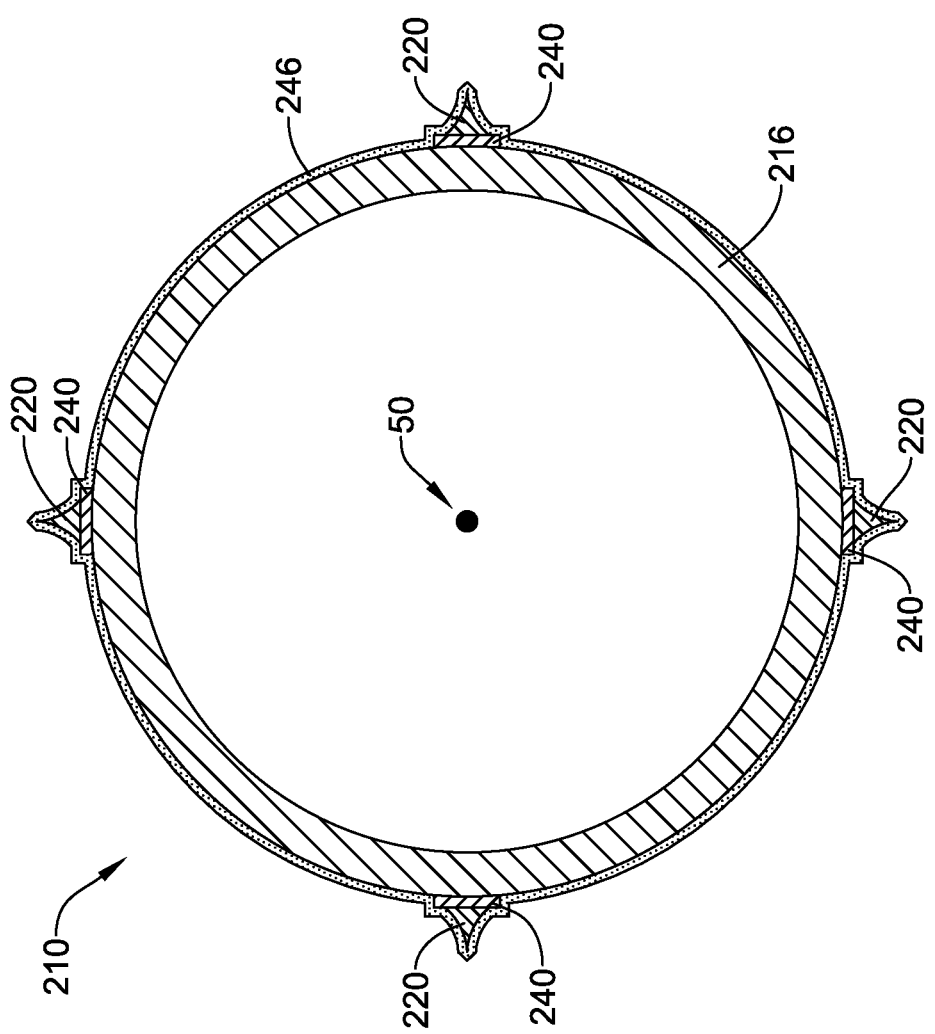
FIG. 7 is a cross-sectional view of another example cutting balloon.

FIG. 7 illustrates another example cutting balloon 210. The cutting balloon 210 may be similar in form and function to other cutting balloons described above. For example, the cutting balloon 210 may include cutting members 220 (similar to other cutting members discussed above) spaced equidistant around the longitudinal axis 50 of the balloon member 216 (similar to other balloons discussed above). Further, each of the cutting members 220 may be attached to the balloon 216 via a mounting pad 240 and attachment material (not shown in FIG. 7). Additionally, the cutting balloon 210 may include a covering 246 disposed along the balloon 216, the cutting members 220, the mounting pads 240 and/or other structures of the cutting balloon 210. The covering 246 may be similar to the covering 146 described above. However, FIG. 7 illustrates that, in some instances, the cutting balloon 210 may not include fibers attached to the balloon 216.

The cutting balloon 10/110/210 and/or other components of the cutting balloon 10/110/210 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the cutting balloon 10/110/210 and/or other components of the cutting balloon 10/110/210 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the cutting balloon 10/110/210 and/or other components of the cutting balloon 10/110/210 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the cutting balloon 10 and/or other components of the cutting balloon 10/110/210 to achieve the same result.

In some embodiments, a degree of Magnetic Resonance Imaging (MRI) compatibility is imparted into the cutting balloon 10/110/210 and/or other components of the cutting balloon 10/110/210. For example, the cutting balloon 10/110/210 and/or other components of the cutting balloon 10/110/210, or portions thereof, may be made of a material that does not substantially distort the image and create substantial artifacts (e.g., gaps in the image). Certain ferromagnetic materials, for example, may not be suitable because they may create artifacts in an MRI image. The cutting balloon 10/110/210 and/or other components of the cutting balloon 10/110/210, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A cutting balloon, comprising:
    an expandable member having an outer surface and longitudinal axis;
    a mounting pad secured to the outer surface of the expandable member with adhesive;
    a first cutting member attached to the mounting pad on the outer surface of the expandable member; and
    a covering encapsulating the expandable member, the first cutting member, the mounting pad, and the adhesive, wherein the covering, the adhesive, and the mounting pad combine to form a monolithic structure defining a chamber encapsulating the first cutting member.

2. The cutting balloon of claim 1, wherein the covering is fixedly attached to the expandable member, the first cutting member or both the expandable member and the first cutting member.

3. The cutting balloon of claim 1, wherein the covering has a thickness between 5 µm and 35 µm.

4. The cutting balloon of claim 1, wherein the covering includes a thermoplastic polyurethane.

5. The cutting balloon of claim 1, further comprising a plurality of fiber members encapsulated in the expandable member.

6. The cutting balloon of claim 1, wherein the adhesive is thermoplastic polyurethane.

7. The cutting balloon of claim 1, wherein the mounting pad includes a thermoplastic polyurethane.

8. The cutting balloon of claim 1, wherein the covering encapsulates the cutting member, the mounting pad, the adhesive and a portion of the outer surface of the expandable member extending away from the mounting pad.

9. The cutting balloon of claim 1, wherein the expandable member is configured to shift from a first configuration to an expanded configuration, and wherein the covering encapsulates the first cutting member in both the first configuration and the expanded configuration.

10. The cutting balloon claim 1, further comprising a second cutting member disposed along the outer surface of the expandable member, wherein the second cutting member is axially aligned with the first cutting member, and wherein the coating encapsulates the first cutting member, the second cutting member and the expandable member.

11. The cutting balloon of claim 10, wherein the first cutting member and the second cutting member are both attached to the mounting pad.

12. The cutting balloon of claim 1, wherein the covering is configured to prevent the cutting member from releasing from the outer surface of the expandable member.

13. A cutting balloon, comprising;
an expandable member having an outer surface and a longitudinal axis, the expandable member configured to shift between a first configuration to a second expanded configuration;
a cutting member assembly attached to the outer surface of the expandable member, the cutting member assembly including:
an adhesive disposed along the outer surface of the expandable member;
a mounting pad attached to the attachment material; and
a cutting blade attached to the mounting pad;
a covering fixedly attached to both the expandable member and the cutting member assembly, wherein the covering surrounds both the expandable member and the cutting member assembly as the expandable member shifts between the first configuration and the second configuration, wherein the covering, the adhesive, and the mounting pad combine to form a monolithic structure defining a chamber encapsulating the cutting blade.

14. The cutting balloon of claim 13, wherein the covering is configured to prevent the cutting member from releasing from the outer surface of the expandable member.

15. The cutting balloon of claim 13, wherein the covering has a thickness between 5 µm and 35 µm.

16. The cutting balloon of claim 13, wherein the covering includes a thermoplastic polyurethane.

17. A method of treating a body lumen, the method comprising:
advancing a cutting balloon to a target site in the body lumen, the cutting balloon including:
an expandable member having an outer surface and longitudinal axis;
a mounting pad secured to the outer surface of the expandable member with adhesive;
a first cutting member attached to the mounting pad on the outer surface of the expandable member; and
a covering encapsulating the expandable member, the first cutting member, the mounting pad, and the adhesive, wherein the covering, the adhesive, and the mounting pad combine to form a monolithic structure defining a chamber encapsulating the first cutting member;
expanding the expandable member such that the cutting member engages the target site.

* * * * *